United States Patent
Choi et al.

(10) Patent No.: US 7,521,477 B2
(45) Date of Patent: Apr. 21, 2009

(54) VITAMIN C DERIVATIVES WITH PEPTIDE, PREPARATION METHOD THEREOF AND COMPOSITION COMPRISING THE SAME

(75) Inventors: Ho Il Choi, Daejeon (KR); Sun Young Kim, Daejeon (KR); Heung Jae Kim, Daejeon (KR); Jung Woo Choi, Daejeon (KR)

(73) Assignee: Peptron Co., Ltd. (KR)

( * ) Notice: Subject to any disclaimer, the term of this patent is extended or adjusted under 35 U.S.C. 154(b) by 0 days.

(21) Appl. No.: 10/554,667

(22) PCT Filed: Apr. 7, 2004

(86) PCT No.: PCT/KR2004/000804

§ 371 (c)(1),
(2), (4) Date: Nov. 24, 2006

(87) PCT Pub. No.: WO2004/096837

PCT Pub. Date: Nov. 11, 2004

(65) Prior Publication Data

US 2007/0093425 A1    Apr. 26, 2007

(30) Foreign Application Priority Data

Apr. 30, 2003  (KR) .................. 10-2003-0027735
Mar. 18, 2004  (KR) .................. 10-2004-0018506

(51) Int. Cl.
*A61K 31/34*    (2006.01)
*A61K 38/06*    (2006.01)

(52) U.S. Cl. .................. 514/474; 549/315; 530/330; 530/331

(58) Field of Classification Search .................. 514/474; 549/315; 530/330, 331
See application file for complete search history.

(56) References Cited

U.S. PATENT DOCUMENTS 4,665,054 A    5/1987    Pickart
4,983,382 A    1/1991    Wilmott 5,409,693 A    4/1995    Perricone

FOREIGN PATENT DOCUMENTS

WO    WO 9103488    3/1991
WO    WO 9107431    5/1991

OTHER PUBLICATIONS

Makino, Y., et al. "Induction of cell death by ascorbic acid derivatives in human renal carcinoma and glioblastoma cell lines" Anticancer Res., 1999, vol. 19(4B): pp. 3125-3132.
Darr, D. et al., "Effectiveness of antioxidants (vitamins C and E) with and without sunscreens as topical photoprotectants" 1996, Acta Derm. Venereol. (Strckh). 76: 264-268.
Black, H. S. et al., 1975, "Suppression of ultraviolet light-induced tumor formation by dietary antioxidants" J. Invest. Dermatol. 65: 412-414.
Darr, D. et al., "Topical vitamin C protects porcine skin from ultraviolet radiation-induced damage" 1992, Br. J. Dermatol. 127: 247-253.
Buettner, G. R. et al. "Chemistry and Biochemistry of Ascorbic Acid," 1996. Handbook of antioxidants. pp. 91-115.
Tomita, Y. et al., "Inactivation of tyrosinase by dopa" 1980, J. Invest. Dermatol. 75(5): 379-382.
Nakamura, T. et al., "Vitamin C abrogates the deleterious effects of UVB radiation on cutaneous immunity by a mechanism that does not depend on TNF-alpha" 1997, J. Invest. Dermatol. 190: 20-24.
Bissett, D. et al., "Photoprotective effect of superoxide-scavenging antioxidants against ultraviolet radiation-induced chronic skin damage in the hairless mouse" 1990, Photodermatol Photoimmunol Photomed 7: 56-62.
Kou Katayama et al., 1993, "A pentapeptide from type I procollagen promotes extracellular matrix production" The Journal of Biological Chemistry 268(14): 9941-9944.
Pinnell, S. R. et al., "Topical L-ascorbic acid: percutaneous absorption studies" 2001. Dermatologic Surgery. 27(2): 137-142.
Shuster S., et al. "The influence of age and sex on skin thickness, skin collagen and density" 1975, British Journal of Dermatology, 93(6): 639-643.
Kou Katayama et al., "Regulation of extracellular matrix production by chemically synthesized subfragments of type I collagen carboxy propeptide" 1991, Biochemistry 30: 7097-7104.

*Primary Examiner*—David Lukton
(74) *Attorney, Agent, or Firm*—Casimir Jones, S.C.

(57) ABSTRACT

Disclosed are vitamin C derivatives linked with a peptide or a pharmaceutically acceptable salt thereof, a method of preparing the same, and a composition comprising the same.

9 Claims, 4 Drawing Sheets

VITAMIN C DERIVATIVES WITH PEPTIDE, PREPARATION METHOD THEREOF AND COMPOSITION COMPRISING THE SAME

This application is a 371 of PCT/KR04/00804, filed Apr. 7, 2004, which claims priority to KR 10-2003-0027735, filed Apr. 30, 2003, and KR 10-2004-0018506, filed Mar. 18, 2004.

BACKGROUND OF THE INVENTION

1. Field of the Invention

The present invention relates to vitamin C derivatives linked with a peptide(s) or pharmaceutically acceptable salts thereof, a method of preparing the same, and a composition comprising the same.

2. Description of the Prior Art

The skin is the largest organ of the body, and has several different functions. In detail, the skin protects the body from bacterial invasion and chemicals in the outside world, provides a mechanical barrier to protect the body, regulates body temperature and eliminates waste products, and serves as an organ of respiration. The skin has three layers: the epidermis, the dermis and the subcutaneous tissues. The epidermis, the outer part of the skin, is the thinnest layer of the skin and includes keratinocytes and melanocytes, which are closely associated with each other. The dermis, which is the inner layer of the skin, occupies about 95% of the skin, and is responsible for regulating the moisture levels of the skin and protecting the skin. The dermis comprises a tight, sturdy mesh of collagen and elastin fibers. Both collagen and elastin are the representative proteins playing a critical role in skin resilience (wrinkling of the skin). Also, the dermis is the site where blood vessels and nerves are located, and contains fat cells and the natural moisturizer, Na-PCA or hyaluronic acid. The subcutaneous tissue, which is the innermost layer of the skin, functions to supply nutrients to the epidermis and the dermis, determine body shape, control body temperature, absorbs external impacts, protect cells under the subcutaneous tissue, etc.

However, the normal skin functions are rapidly lost with time by intrinsic or environmental factors, causing the skin to appear as aged. As skin aging proceeds, the skin's constituents, the epidermis, the dermis and the subcutaneous tissue become thin while the collagen and elastin fibers become slender and less elastic, leading to a reduction in skin resilience and eventually causing generation of wrinkles. In addition, as the lipid barrier, which serves as a skin barrier, undergoes a change in lipid content and composition, the skin has physiological changes including a reduced moisture level and increased dryness. Further, chloasma, freckles, pigmentation and other skin lesions are caused with skin aging.

In order to solve these problems associated with skin aging, many studies are performed to find or develop compounds having skin improving effects and compositions containing the compounds as effective ingredients.

Vitamin C, vitamin E, beta-carotene and other antioxidants are widely used for inhibiting skin aging. Of them, vitamin C (ascorbic acid) has an antioxidant effect as well as other various effects of protecting the skin from ultraviolet (UV) exposure, reducing wrinkling of the skin by stimulating collagen synthesis, lightening pigmentation such as chloasma, freckles and black spots, and reinforcing the immune system. The functions of vitamin C will be described in detail, below.

Vitamin C protects the skin from UV radiation, in particular, ultraviolet A (UVA) radiation (Darr, D. et al., 1996, Acta Derm. Venereol. (Strckh). 76: 264-268; Black, H. S. et al., 1975, J. Invest. Dermatol. 65: 412-414). Also, vitamin C functions to protect the skin from damage caused by ultraviolet B (UVB) radiation. When vitamin C is applied to some regions of the skin of pig and human subjects before UVB radiation, the redness (erythema) and sun burn are prevented (Darr, D. et al., 1992, Brit. J. Dermatil. 127: 247-253; Murry, J. et al., 1991, J. Invest. Dermatol. 96: 587).

In the skin, blood and other tissues, vitamin C serves as a potent in vivo antioxidant that neutralizes reactive oxygen species (ROS) generated by chemical contamination, smoking, or, in particular, UV light. This action of vitamin C is possible due to its chemical structure of easily oxidizing to dehydro-L-ascorbic acid by accepting two electrons. Vitamin C is a key element of the non-enzymatic antioxidant protection system of the skin. At high concentrations, vitamin C functions to neutralize ROS, such as singlet oxygen, superoxide anion and hydroxy radicals, before they oxidize or denature proteins, nucleic acids, membrane lipids and other biological components (Buettner, G. R. et al. 1996. Cadenas, E., Packer, L., eds. Handbook of antioxidants. pp. 91-115).

When transdermally applied to the stratum corneum of the skin, vitamin C was demonstrated to have skin appearance benefits including enhancements in luster, tone and elasticity, and reductions in wrinkles, etc. by stimulating collagen synthesis (U.S. Pat. No. 4,983,382). Biosynthesis of hydroxyproline amounting to about 10% of amino acid residues of a collagen polypeptide is stimulated by proline hydroxylase. Vitamin C acts as a cofactor of the proline hydroxylase enzyme (Tomita, Y. et al., 1980, J. Invest. Dermatol. 75(5): 379-382). That is, vitamin C has skin appearance-improving effects such as anti-wrinkling by stimulating synthesis of hydroxyproline via stimulation of the activity of proline hydroxylase and finally increasing biosynthesis of collagen with a triple helix structure.

Vitamin C has a whitening effect by inhibiting tyrosinase known to play a critical role in melanin synthesis and eventually reducing melanin production (Tomita, Y. et al., 1980, J. Invset. Dermatol. 75(5); 379-382).

As described above, vitamin C reinforces the immune system. In particular, vitamin C was proven to inhibit the release of histamine from cellular membranes, thereby reducing allergic responses on sensitive skin, and protects mice from UV-induced immunosuppression and tolerance upon skin contact with an antigen (Nakamura, T. et al., 1997, J. Invest. Dermatol. 109: 20-24). In addition, vitamin C inhibits viral infections by stimulating phagocytosis by leukocytes and leukocyte migration during viral infection, and increases the biosynthesis of interferon as a substance inhibiting the viral proliferation. In addition to the functions as noted above, vitamin C participates in the metabolism of folic acid and amino acids.

Vitamin C, which has the diverse functions as described above, is a water-soluble substance having a chemical formula of $C_6H_8O_6$. The hydrophilicity of vitamin C is attributed to hydroxyl groups at carbon positions 2, 3, 5 and 6 of the molecule. At a neutral pH, such as in water, these hydroxyl groups, particularly the groups at carbon positions 2 and 3, carry negative charges. The negative charges allow vitamin C to be dissolved quickly and completely in an aqueous solution, but greatly limit the solubility of the molecule in a non-aqueous, organic environment such as the skin. Also, vitamin C at neutral pH also does not dissolve well in organic solvents commonly used in formulations for topical use, such as glycerin, propylene glycol, and various fats, thus limiting the usefulness of organic solvents as a vehicle for carrying vitamin C into the skin. That is, when vitamin C is not ionized, its absorption into the skin barrier can be easily achieved. This non-ionic state occurs only at a pH of less than 4.2.

When vitamin C is topically applied, its accumulation in the skin proved to be 20 to 40-fold higher than the cases of being orally administered. When vitamin C is topically applied, with aims of utilizing its antioxidant effect, protecting the skin from UV exposure, improving wrinkling of the skin by stimulation of collagen synthesis, lightening pigmentation such as chloasma, freckles and black spots, and reinforcing the immune system, the effective substance should pass through the outermost stratum corneum of the skin and arrive the place where cells exist in the epidermis, and, for this, should have a high percutaneous absorption rate. Typically, the percutaneous permeability of a certain substance is related with the lipophilicity of the substance. When the substance has a lipophilicity similar to the skin, it has a higher distribution coefficient into the skin, and thus, easily absorbed through the skin. However, due to its high hydrophilicity, vitamin C has a low distribution into the skin, and thus, is difficult to be percutaneously absorbed.

Many attempts were made to improve the instability and the low percutaneous absorption of vitamin C having diverse effects as described above.

Derivatives of vitamin C are classified into three types, as described below. One type includes phosphorylated ascorbic acid or metal salts thereof. Ester linkage of a hydroxyl group at a carbon position 2 or 3 of ascorbic acid and a phosphate group results in production of ascorbyl-2-phosphate or ascorbyl-3-phosphate. These derivatives of vitamin C are, unlike other derivates, easily converted to L-ascorbic acid, the only form of vitamin C that can be used by the body, but has a significant problem of being difficult to be absorbed into the skin due to their negative charges.

Another type of vitamin C derivatives includes fatty acid-linked forms of ascorbic acid. For example, U.S. Pat. No. 5,409,693 discloses fat soluble fatty acid esters of ascorbic acid, for example, ascorbyl palmitate, ascorbyl laurate, ascorbyl myristate and ascorbyl stearate. Of them, ascorbyl-6-palmitate is the most widely used. Ascorbyl-6-palmitate is easily absorbed into the skin, but is difficult to be converted to L-ascorbic acid. Ascorbyl-6-palmitate was reported to fail to protect mouse skin from photo-oxidation (Bissett, D. et al., 1990, Photodermatol Photoimmunol Photomed 7: 56-62). Also, when a serum containing 10 wt % of ascorbyl-6-palmitate was applied to pig skin, no significant increase in skin levels of ascorbic acid was observed (Pinnell, S. R. et al., 2001. Dermatologic Surgery. 27(2): 137-142).

The third type of vitamin C derivatives includes monosaccharide esters of ascorbic acid, for example, glycosylated, mannosylated, fructosylated, fucosylated, galactosylated, N-acetylglucosaminated, and N-acetylmuramic derivatives of ascorbic acid. However, they have not been concretely and accurately evaluated for in vivo physiological activity.

Collagen is very abundant in the skin, blood vessels, intestine, bone, etc, and makes up 70% of the dermis of the skin. Also, the epimysium surrounding the muscle is composed of collagen. Collagen, which makes up 30% of the total weight of body proteins, provides mechanical strength to the skin, strength with resistance to tearing and stretching to the connective tissue and cohesion to the tissues, and functions to maintain cell adherence and induce cell division and differentiation upon growth of organisms or wound healing. Collagen is synthesized in the fibroblasts. Its levels are reduced by intrinsic aging and photoaging, and are known to be reduced by 65% during the ages ranging from 20 to 80 (Shuster S., 1975, British Journal of Dermatology, 93(6): 639-643). Active synthesis of collagen in vivo results in an increase in the levels of dermal substrate components, which is responsible for wound healing, increased skin elasticity, reduced wrinkles, and the like. With this identification, collagen is used in cosmetic products, foods, medicinal products, etc. As a minimal active unit of collagen, an oligopeptide consisting of less than 10 amino acids serves as a messenger, a stimulator and a nerve impulse transmitter, and involved in physiological events, such as, growth control, lactation, immunity, digestion, increased blood pressure and wound healing. Some peptides are identified to have wound healing effects, as disclosed in France Pat. No. 2,668,265, U.S. Pat. No. 4,665,054, and International Pat. Publication Nos. W091/3488 and W091/7431. However, these peptides have a disadvantage of causing a great reduction in product stability due to their property to form a precipitate in a composition.

SUMMARY OF THE INVENTION

In order to overcome the problems of the conventional vitamin C derivatives, the present invention aims to provide vitamin C derivatives with improved safety and stability and excellent percutaneous permeability by linking vitamin C with a peptide.

BRIEF DESCRIPTION OF THE DRAWINGS

The above and other objects, features and other advantages of the present invention will be more clearly understood from the following detailed description taken in conjunction with the accompanying drawings, in which.

DETAILED DESCRIPTION OF THE INVENTION

Figure 1:
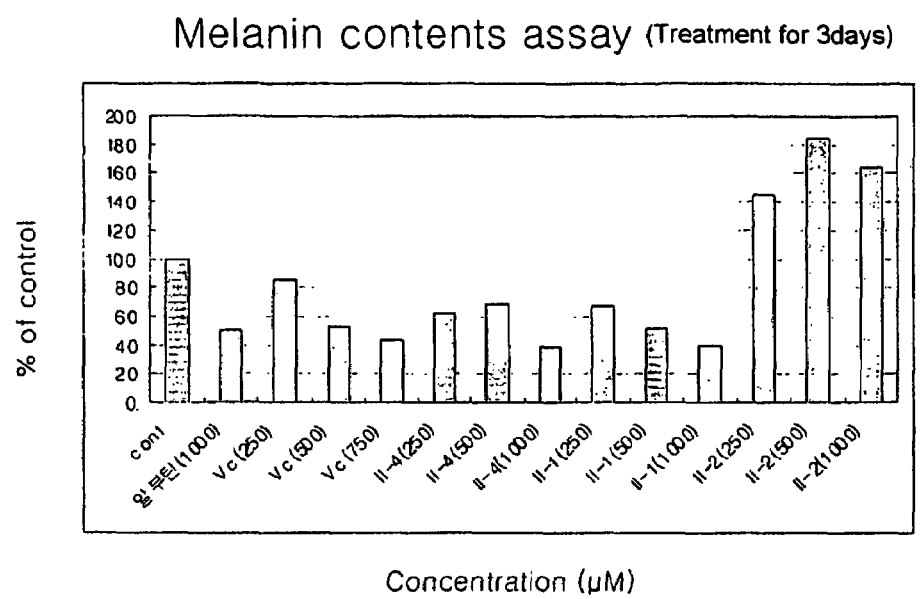
FIG. 1 is a graph showing the effects of the compounds of the present invention, vitamin C and arbutin on melanin production by B16 melanocytes.

In an aspect, the present invention relates to a vitamin C derivative represented by Chemical Formula 1, below, or a pharmaceutically acceptable salt thereof.

[Chemical Formula 1]

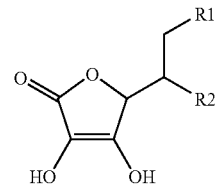

wherein, R1 and R2, which are identical or different, each represent —OH or

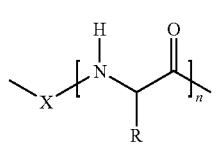

but both are not —OH simultaneously, wherein, X represents —OC(O) (CH$_2$)mC(O)—,

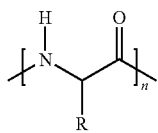

is a peptide in which identical or different amino acid residues selected from natural or unnatural amino acids are joined by amide linkages, R is a side chain of each of the natural or unnatural amino acid residues, n is an integer of 3 to 10, and m is an integer of 2 to 5.

In detail, the compound of Chemical Formula 1 includes the compounds of the following Chemical Formulas 1a, 1b and 1c:

[Chemical Formula 1a]

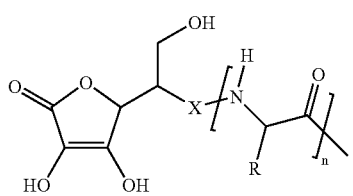

[Chemical Formula 1b]

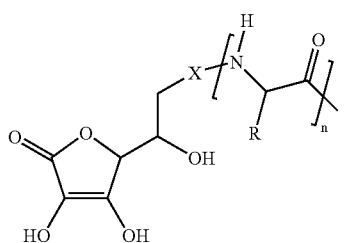

[Chemical Formula 1c]

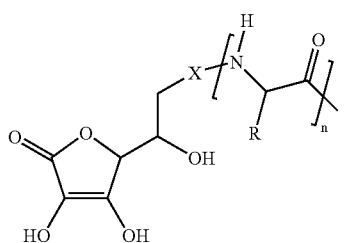

In a preferred aspect,

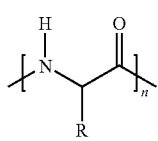

is a peptide in which identical or different amino acid residues selected from glycine, lysine, histidine, serine, proline, hydroxyproline and threonine are joined by amide linkages, wherein R is a side chain of each of the above amino acid residues and n is an integer of 3 and 7, more preferably, an integer of 3 to 5, so that

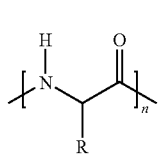

is more preferably a tri-, tetra- or penta-peptide, and particularly preferably, glycyl-lysyl-histidine, glycyl-histidyl-lysine, glycyl-prolyl-hydroxyproline or lysyl-threonyl-threonyl-lysyl-serine. In addition, m is an integer of 2 to 4, more preferably, an integer of 2 or 3, and particularly preferably, an integer of 2, so that X is succinyl.

In another aspect, the present invention relates to a vitamin C derivative represented by Chemical Formula 2, below, or a pharmaceutically acceptable salt thereof.

[Chemical Formula 2]

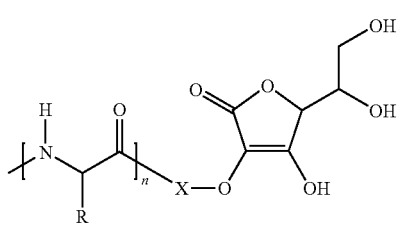

wherein, X is —(CH$_2$)pO—, and

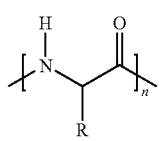

is a peptide in which identical or different amino acid residues selected from natural or unnatural amino acids are joined by amide linkages, wherein, R is a side chain of each of the natural or unnatural amino acid residues, n is an integer of 3 to 10, and p is an integer of 2 to 5.

In a preferred aspect,

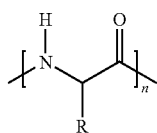

is a peptide in which identical or different amino acid residues selected from glycine, lysine, histidine, serine, proline, hydroxyproline and threonine are joined by amide linkages, wherein R is a side chain of each of the above amino acid residues and n is an integer of 3 to 7, more preferably, an integer of 3 to 5, so that

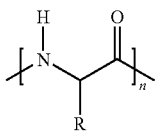

is more preferably a tri-, tetra or penta-peptide, and particularly preferably, glycyl-lysyl-histidine, glycyl-histidyl-lysine, glycyl-prolyl-hydroxyproline or lysyl-threonyl-threonyl-lysyl-serine (SEQ ID NO:1). In addition, p is an integer of 2 to 4, more preferably, an integer of 3 or 4, and particularly preferably, an integer of 3, so that X is propanol.

In a preferred aspect, the compound of the present invention is selected from the group consisting of 6-(succinyl-lysyl-threonyl-threonyl-lysyl-serine(SEQ ID NO:1))ascorbic acid, 5-(succinyl-lysyl-threonyl-threonyl-lysyl-serine) ascorbic acid, 5,6-di(succinyl-lysyl-threonyl-threonyl-lysyl-serine(SEQ ID NO:1))ascorbic acid, 6-(succinyl-glycyl-lysyl-histidine)ascorbic acid, 5-(succinyl-glycyl-lysyl-histidine)ascorbic acid, 5,6-di(succinyl-glycyl-lysyl-histidine)ascorbic acid, 6-(succinyl-glycyl-histidyl-lysine) ascorbic acid, 5-(succinyl-glycyl-histidyl-lysine)ascorbic acid, 5,6-di(succinyl-glycyl-histidyl-lysine)ascorbic acid, 6-(succinyl-glycyl-prolyl-hydroxyproline)ascorbic acid, 5-(succinyl-glycyl-prolyl-hydroxyproline)ascorbic acid, 5,6-(succinyl-glycyl-prolyl-hydroxyproline)ascorbic acid, 2-(propyl-lysyl-threonyl-threonyl-lysyl-serine(SEQ ID NO:1))ascorbic acid, 2-(propyl-glycyl-lysyl-histidine)ascorbic acid, 2-(propyl-glycyl-histidyl-lysine)ascorbic acid, 2-(propyl-glycyl-prolyl-hydroxyproline)ascorbic acid, and pharmaceutically acceptable salts thereof.

In a most preferred aspect, the compound of the present invention is selected from the group consisting of 6-(succinyl-lysyl-threonyl-threonyl-lysyl-serine(SEQ ID NO:1)) ascorbic acid, 6-(succinyl-glycyl-lysyl-histidine)ascorbic acid, 6-(succinyl-glycyl-histidyl-lysine)ascorbic acid, and pharmaceutically acceptable salts thereof.

The term "natural amino acid", as used herein, means an α-amino acid that is selected from the group consisting of alanine, valine, leucine, isoleucine, proline, phenylalanine, tryptophan, methionine, glycine, serine, threonine, cysteine, tyrosine, asparagine, glutamine, lysine, arginine, histidine, aspartic acid and glutamic acid. In addition, the term "unnatural amino acid", as used herein, means an amino acid for which there is no nucleic acid codon. Examples of unnatural amino acids include, for example, the D-isomers of the natural α-amino acids as indicated above; aminobutyric acid (Aib), 3-aminoisobutyric acid (bAib), norvaline (Nva), β-Ala, 2-aminoadipic acid (Aad), 3-aminoadipic acid (bAad), 2-aminobutyric acid (Abu), γ-aminobutyric acid (Gaba), 6-aminocaproic acid (Acp), 2,4-diaminobutryic acid (Dbu), α-aminopimelic acid, trimethylsilyl-Ala (TMSA), allo-isoleucine (alle), norleucine (Nle), tert-Leu, citrulline (Cit), ornithine (Orn), 2,2'-diaminopimelic acid) (Dpm), 2,3-diaminopropionic acid (Dpr), (α- or β-Nal, cyclohexyl-Ala (Cha), hydroxyproline, sarcosine (Sar), and the like; cyclic amino acids; $N^\alpha$-alkylated amino acids such as $N^\alpha$-methylglycine (MeGly), $N^\alpha$-ethylglycine (EtGly) and $N^\alpha$-ethylasparagine (EtAsn); and amino acids in which the α-carbon bears two side-chain substituents.

The term "peptide", as used herein, means a polymer in which the monomers are three to ten amino acid residues joined together through amide bonds (or peptide bonds). The peptide may be prepared by isolating proteins from a biological sample and digesting the proteins with a proteinase into low molecular weight fragments, or by employing a genetic recombination technique and a protein expression system. Preferably, the peptide is prepared by in vitro synthesis, for example, using a peptide synthesizer. If desired, the peptide may be a derivative thereof having a substitution of a particular atom or atom unit with, for example, a hydroxyl group. In a peptide, a COOH group and a $NH_2$ group are designated "C-terminus"and "N-terminus", respectively.

In the present invention, the peptide includes, in particular, a collagen peptide. The "collagen peptide"is a fragment of a collagen protein, which may be used for stimulating collagen synthesis or as a constituent of the collagen protein. For example, tri- to penta-peptides used in the practice of the present invention have the effects of providing appropriate moisture to the skin and smoothing skin wrinkles by stimulating synthesis of collagen and glycoseaminoglycan that are abundantly present in the dermal layer of the skin and thus enhancing the moisture retaining efficiency of the skin and the elasticity of the dermis. In particular, a penta-peptide, lysyl-threonyl-threonyl-lysyl-serine(SEQ ID NO:1), which is a carboxyl terminal fragment of type I collagen that is responsible for the formation of the skin connective tissue and wrinkles and the skin's moisture, was reported to stimulate the synthesis of types I and II collagen upon culturing of fibroblasts synthesizing collagen, fibronectin responsible for intercellular communication involved in cell-cell adhesion, and a growth factor, β-TGF (Kou Katayama et al., 1991, Biochemistry 30: 7097-7104), and was reported to bind to transcription of a collagen gene by binding to the promoter of the collagen gene (Kou Katayama et al., 1993, The Journal of Biological Chemistry 268(14): 9941-9944).

Korean Pat. Application No. 10-2001-0060244 discloses a vitamin C derivative linked with a HIV protein, Tat peptide. In this application, the Tat peptide is directly (without use of a linker) ester-linked to a hydroxyl group at C2 or C3 of vitamin C, or ether-linked to a hydroxyl group at C2 or C3 of vitamin C via an alcohol having 6 or higher carbon atoms, for example, a —$(CH_2CH_2O)_3$— linker. This vitamin C derivative has a distinct chemical structure from the present vitamin C derivative in which a collagen peptide is ether-linked to vitamin C via an alcohol having 5 or less carbon atoms, —$(CH_2)_{2-5}$—O— linker and the peptide is ester-linked to the linker. When a collagen peptide is linked to vitamin C by an ester bond, it is easily separated from the vitamin C in vivo in comparison with the case of being linked to the vitamin C by an ether bond.

The term "pharmaceutically acceptable salt", as used herein, includes those which are induced from pharmaceutically acceptable inorganic and organic acids. Examples of suitable acids may include hydrochloric acid, bromic acid, sulfuric acid, nitric acid, perchloric acid, fumaric acid, maleic acid, phosphoric acid, glycolic acid, lactic acid, salicylic acid, succinic acid, toluene-p-sulfonic acid, tartaric acid, acetic acid, citric acid, methanesulfonic acid, formic acid, benzoic acid, malonic acid, naphthalene-2-sulfonic acid, and benzenesulfonic acid. Salts induced from suitable bases may include alkali metals, for example, sodium, and alkali earth metals, for example, magnesium, ammonium, and the like.

In a further aspect, the present invention relates to a method of preparing a vitamin C derivative of Chemical Formula 1 or a pharmaceutically acceptable salt thereof, which is characterized by introducing a benzyl group into each of hydroxyl groups at carbon positions 2 and 3 of vitamin C for protection of the hydroxyl group, and ester-linking a hydroxyl group at a carbon position 5 or 6 or at each of both carbon positions 5 and 6 of the vitamin C to dicarboxylic acid having 2 to 5 carbon atoms and then amide-linking to a peptide.

In a preferred aspect, the present invention provides a method of preparing a vitamin C derivative of Chemical Formula 1 or a pharmaceutically acceptable salt thereof, including reacting 5,6-isopropylidiene-ascorbic acid of Chemical Formula 3 with benzyl halide of Chemical Formula 4 to introduce a benzyl group into a hydroxyl group at each of both carbon positions 2 and 3 of the 5,6-isopropylidiene-ascorbic acid; ring-opening 5,6-isopropylidiene-ascorbic acid having benzyl groups of Chemical Formula 5 and reacting the resulting compound with dicarboxylic acid of Chemical Formula 6; amide-linking a compound of Chemical Formula 7 to a peptide of Chemical Formula 8; and removing protection groups from the resulting amide-linked compound.

[Chemical Formula 3]

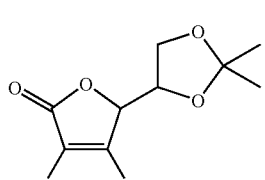

[Chemical Formula 4]

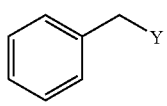

[Chemical Formula 5]

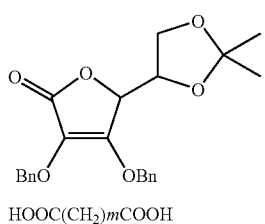

[Chemical Formula 6]

HOOC(CH$_2$)$m$COOH

[Chemical Formula 7]

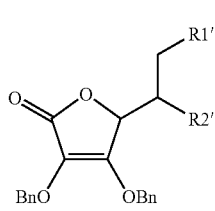

[Chemical Formula 8]

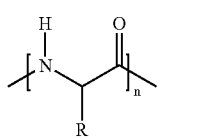

wherein, m is an integer of 2 to 5,
Bn represents benzyl,
Y is chlorine, bromine, fluorine or iodine,
R1' and R2', which are identical or different, each represent —OH or —OC(O) (CH$_2$) mC(O)OH, but are not —OH simultaneously,
R is a side chain of a protected or unprotected, natural or unnatural amino acid residue, and
n is an integer of 3 to 10.

In a more preferred aspect, the 5,6-isopropylidiene-ascorbic acid of Chemical Formula 3 is reacted with the benzyl halide of Chemical Formula 4, preferably, benzyl chloride, at 40° C. to 60° C., preferably, 50° C., for 3 to 5 hrs, preferably, 4 hrs. In detail, the compound of Chemical Formula 5, produced by introduction of benzyl groups into hydroxyl groups at carbon positions 2 and 3 of ascorbic acid, is added with an acid, preferably, trifluoracetic acid, and an incubation follows for 3 to 5 hrs, preferably, 4 hrs, to open the 5,6-isopropylidiene ring. To the resulting ring-opened compound, dicarboxylic acid of Chemical Formula 6, preferably, succinic acid, is added, and an incubation follows at room temperature for 15 to 17 hrs, preferably, 16 hrs to ester-link the ascorbic acid and the succinic acid. The resulting compound of Chemical Formula 7 is amide-linked to a —NH2 group at the N-terminus of a peptide protected by typical solid-phase synthesis on a resin, and protection groups are then removed.

The above reaction is carried out under an anhydrous condition, for example, using an anhydrous organic solvent. Examples of the anhydrous organic solvent include dimethylformamide, dimethylsulfoxide, N-methylpyrollidone and dichloromethane. Preferred is dimethylformamide. In addition, a condensing agent useful in the above reaction includes DCC (N,N'-dicyclohexylcarbodiimide), HOBT (N-hydroxybenzotriazole), PyBOP (benzotriazole-1-yl-oxy-tris-pyrrolidinophosphonium hexafluorphosphate), and HBTU (2-(1H-benzotriazole-1-yl)-1,3,3-tetramethyluronium hexafluorophosphate).

In still another aspect, the present invention relates to a method of preparing a vitamin C derivative of Chemical Formula 2 or a pharmaceutically acceptable salt thereof, which is characterized by introducing a benzyl group into a hydroxyl group at a carbon position 3 of vitamin C for protection of the hydroxyl group, and ether-linking a hydroxyl group at a carbon position 2 of the vitamin C to an alcohol having 2 to 5 carbon atoms and then ester-linking to a peptide.

In a preferred aspect, the present invention provides a method of preparing a vitamin C derivative of Chemical Formula 2 or a pharmaceutically acceptable salt thereof, including reacting 5,6-isopropylidiene-ascorbic acid of Chemical Formula 3 with benzyl halide of Chemical Formula 4 to introduce a benzyl group into a hydroxyl group at a carbon position 3 of the 5,6-isopropylidiene-ascorbic acid; reacting a hydroxyl group at a carbon position 2 of a compound of Chemical Formula 9 with halidealcohol of Chemical Formula 10; ester-linking the 5,6-isopropylidiene-ascorbic acid having an alcoholic group with a C-terminus of an amino acid residue; elongating a peptide chain; and removing protection groups from the resulting compound.

[Chemical Formula 3]

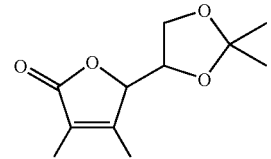

[Chemical Formula 4]

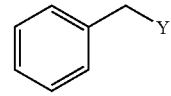

[Chemical Formula 9]

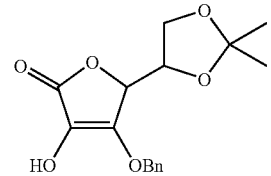

-continued

Y(CH₂)pOH  [Chemical Formula 10]

wherein, p is an integer of 2 to 5;
Bn represents benzyl; and
Y is chlorine, bromine, fluorine or iodine.

In a more preferred aspect, the 5,6-isopropylidiene-ascorbic acid of Chemical Formula 3 is reacted with the benzyl halide of Chemical Formula 4, preferably, benzyl chloride, at 40° C. to 60° C., preferably, 50° C., for 14 to 18 hrs, preferably, 16 hrs. In detail, the compound of Chemical Formula 9, which contains a benzyl group at a hydroxyl group at a carbon position 3, is reacted to the halidealcohol of Chemical Formula 10, preferably, bromopropanol, at 40° C. to 60° C., preferably, 50° C., for 3 to 5 hrs, preferably, 4 hrs, to link the two compounds by an ester bond. The 5,6-isopropylidiene-ascorbic acid having an alcoholic group is then ester-linked to a C-terminus of a protected amino acid residue. Subsequently, a peptide elongation follows, and protection groups are removed from the resulting compound.

The above reaction is carried out under an anhydrous condition, for example, using an anhydrous organic solvent. Examples of the anhydrous organic solvent includes dimethylformamide, dimethylsulfoxide, N-methylpyrollidone and dichloromethane. In addition, a condensing agent useful in the above reaction includes DCC (N,N'-dicycllohexylcarbodiimide), HOBT (N-hydroxybenzotriazole), PyBOP (benzotriazole-1-yl-oxy-tris-pyrrolidinophosphonium hexafluorphosphate), and HBTU (2-(1H-benzotriazole-1-yl)-1,3,3-tetramethyluronium hexafluorophosphate).

A condensing agent, a catalyst and a solvent useful in the present invention include all those which are generally known in the art, and may be used in the range of not negatively affecting a chemical reaction.

The vitamin C derivatives of Chemical Formulas 1 and 2, prepared according to the above methods of the present invention, may be purified by isolation and purification methods known in the art, for example, by recrystallization or column chromatography.

In the present method for preparation of the compound of Chemical Formula 1, as described above, the peptide, which is linked to ascorbic acid hydroxyl groups of which are independently protected with a benzyl group, may be prepared by a solid-phase synthesis method. For example, after each of particular hydroxyl groups of ascorbic acid is protected, a succinyl group is selectively introduced into each of unprotected hydroxyl groups of the ascorbic acid. Then, the ascorbic acid having succinyl groups is reacted with a N-terminus of a peptide synthesized on a resin by a solid-phase synthesis method common in the art, and, subsequently, protection groups of the ascorbic acid and the peptide are removed.

In the present method for preparation of the compound of Chemical Formula 2, as described above, the amino acid residue, which is linked to ascorbic acid hydroxyl groups of which are independently protected with a benzyl group, may be extended by a solid-phase synthesis method. For example, after each of particular hydroxyl groups of ascorbic acid is protected, a propanol group is introduced into each of unprotected hydroxyl groups of the ascorbic acid. Then, the ascorbic acid having propanol groups is reacted with a C-terminus of an amino acid residue on an aqueous phase, peptide elongation is carried out on a resin by a solid-phase synthesis method common in the art, and, subsequently, protection groups of the ascorbic acid and the peptide are removed.

The methods of preparing the compounds of Chemical Formulas 1 and 2 according to the present invention by employing a solid-phase or aqueous-phase synthesis method are schematically shown in Reactions 1 and 2, below. Reaction 1 shows a process of preparing the compound of Chemical Formula 1b. Reaction 2 shows a process of preparing the compound of Chemical Formula 2.

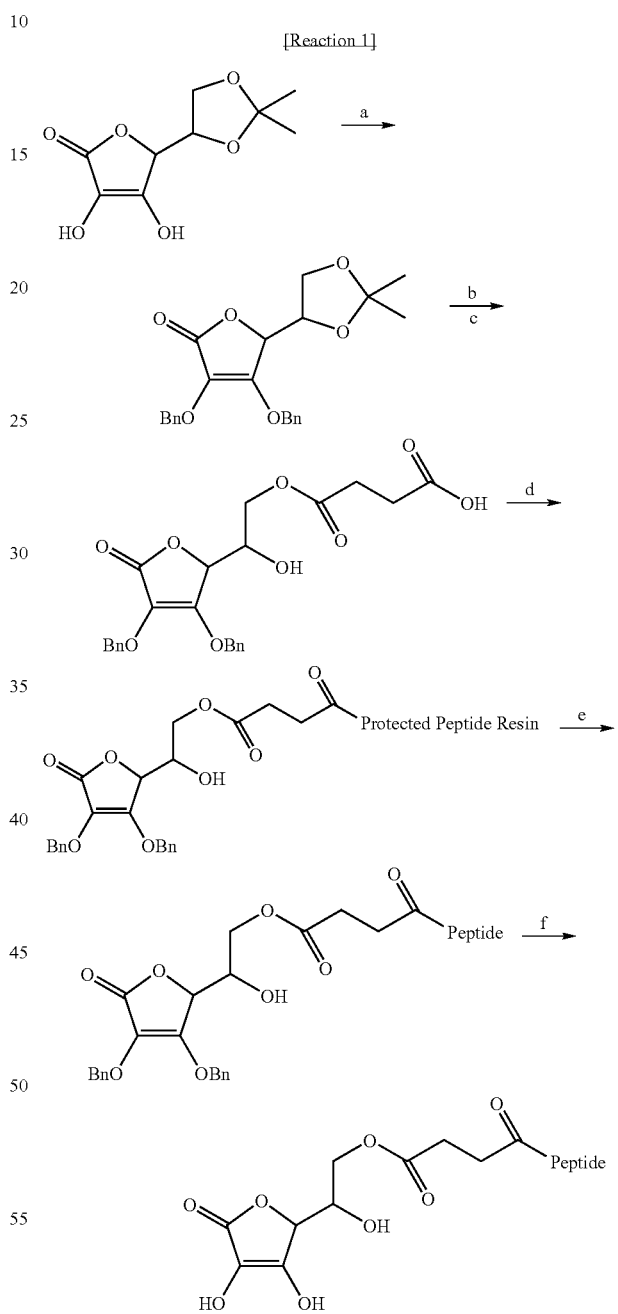

a. BnCl, K₂CO₃, DMF, 50° C., 4 hrs
b. TFA, DCM, room temperature, 4 hrs
c. Succinic anhydride, TEA, DMF, room temperature, 16 hrs
d. Solid-phase synthesis
e. TFA/phenol/thioanisol/H₂O/TIS (85/5/5/3/2)v/v, room temperature, 3 hrs
f. 10% Pd/C, MeOH, H₂, room temperature, 1 hr (BnCl: benzylchloride; DMF: dimethylformamide; TFA: trifluoroacetic acid; DCM: dichloromethane; TEA: triethylamine; MeOH: methanol)

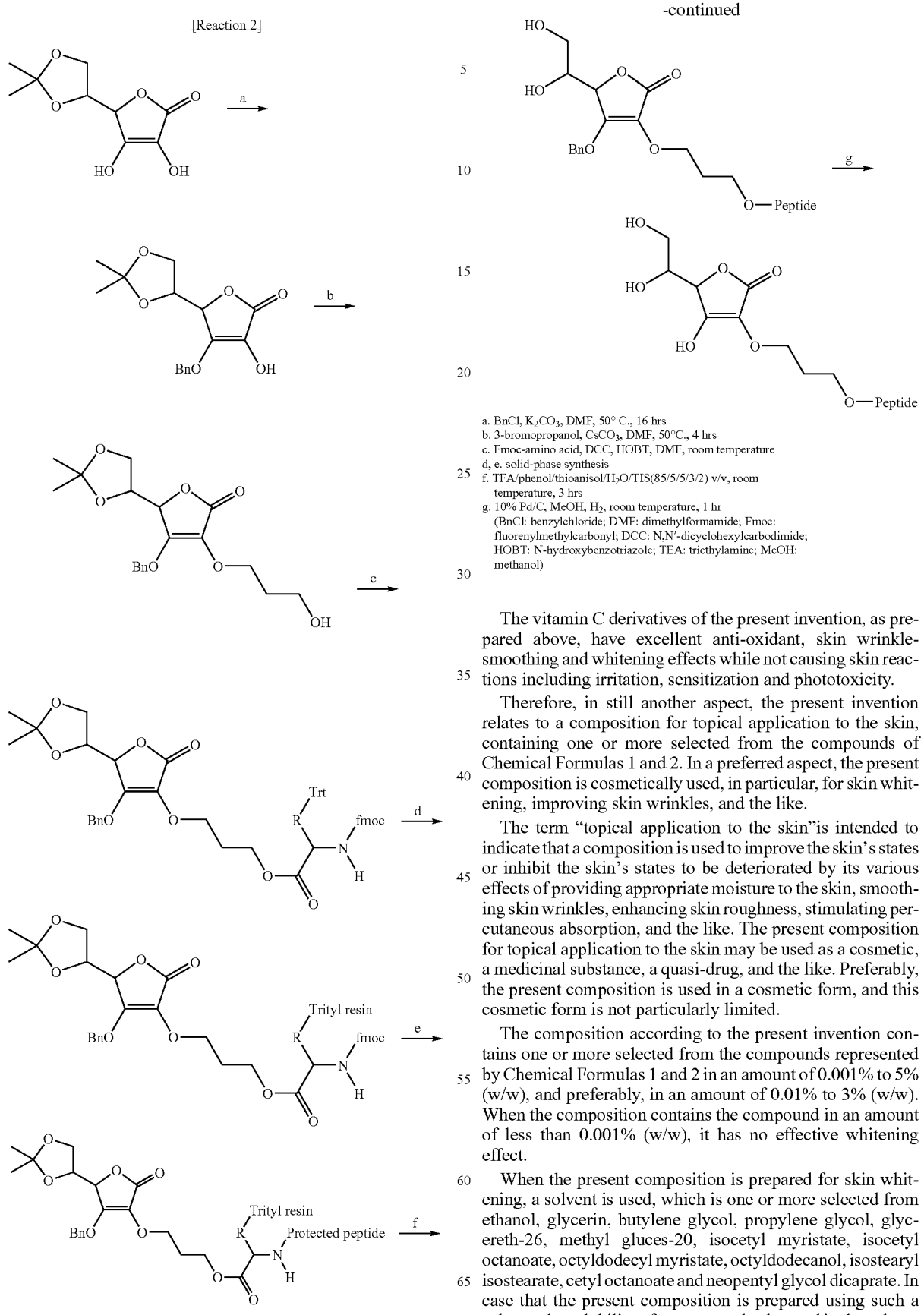

a. BnCl, K$_2$CO$_3$, DMF, 50° C., 16 hrs
b. 3-bromopropanol, CsCO$_3$, DMF, 50°C., 4 hrs
c. Fmoc-amino acid, DCC, HOBT, DMF, room temperature
d, e. solid-phase synthesis
f. TFA/phenol/thioanisol/H$_2$O/TIS(85/5/5/3/2) v/v, room temperature, 3 hrs
g. 10% Pd/C, MeOH, H$_2$, room temperature, 1 hr
(BnCl: benzylchloride; DMF: dimethylformamide; Fmoc: fluorenylmethylcarbonyl; DCC: N,N'-dicyclohexylcarbodiimide; HOBT: N-hydroxybenzotriazole; TEA: triethylamine; MeOH: methanol)

The vitamin C derivatives of the present invention, as prepared above, have excellent anti-oxidant, skin wrinkle-smoothing and whitening effects while not causing skin reactions including irritation, sensitization and phototoxicity.

Therefore, in still another aspect, the present invention relates to a composition for topical application to the skin, containing one or more selected from the compounds of Chemical Formulas 1 and 2. In a preferred aspect, the present composition is cosmetically used, in particular, for skin whitening, improving skin wrinkles, and the like.

The term "topical application to the skin" is intended to indicate that a composition is used to improve the skin's states or inhibit the skin's states to be deteriorated by its various effects of providing appropriate moisture to the skin, smoothing skin wrinkles, enhancing skin roughness, stimulating percutaneous absorption, and the like. The present composition for topical application to the skin may be used as a cosmetic, a medicinal substance, a quasi-drug, and the like. Preferably, the present composition is used in a cosmetic form, and this cosmetic form is not particularly limited.

The composition according to the present invention contains one or more selected from the compounds represented by Chemical Formulas 1 and 2 in an amount of 0.001% to 5% (w/w), and preferably, in an amount of 0.01% to 3% (w/w). When the composition contains the compound in an amount of less than 0.001% (w/w), it has no effective whitening effect.

When the present composition is prepared for skin whitening, a solvent is used, which is one or more selected from ethanol, glycerin, butylene glycol, propylene glycol, glycereth-26, methyl gluces-20, isocetyl myristate, isocetyl octanoate, octyldodecyl myristate, octyldodecanol, isostearyl isostearate, cetyl octanoate and neopentyl glycol dicaprate. In case that the present composition is prepared using such a solvent, the solubility of a compound to be used in the solvent may vary depending on the kind of the compound and a ratio of the solvent and the compound, but any one skilled in the art is able to suitably select and apply the kind and the amount of a solvent to be used according to the nature of a desired product.

The present composition may be formulated into a cosmetic form, such as an ointment for topical application to the skin, a skin softner, a lotion, a nourishing cream, an essence and a pack. The ointment for topical application to the skin may contain the compound of Chemical Formula 1 or 2 as an effective ingredient, as well as 50.0 to 97.0 wt % of Vaseline and 0.1 to 5.0 wt % of polyoxyethylene oleyl-ether phosphate. The skin softner may contain 1.0 to 10.0 wt % of multivalent alcohols, such as propylene glycol, glycerine, etc., and 0.05 to 2.0 wt % of surfactants, such as polyethylene oleyl ether, polyoxyethylene hardened castor oil, etc. In addition to the compound of Chemical Formula 1 or 2 as an effective ingredient, the lotion and nourishing cream may contain 5.0 to 20.0 wt % of oils, such as squalene, Vaseline, octyldecanol, etc., and 3.0 to 15.0 wt % of waxes, such as ethanol, stearyl alcohol, bees wax, etc., the essence may contain 5.0 to 30.0 wt % of multivalent alcohols, such as glycerin, propylene glycol, etc. The massage cream, in addition to the compound of Chemical Formula 1 or 2 as an effective ingredient, may contain 30.0 to 70.0 wt % of oils, such as liquid paraffin, Vaseline, isononyl isononanoate, etc. Also, the pack is prepared in the form of a peel-off pack containing 5.0 to 20.0 wt % of polyvinyl alcohol, or in the form of a wash-off pack prepared by adding 5.0 to 30.0 wt % of pigments, such as caroline, talc, zinc oxide, titanium dioxide, etc., to a general cosmetic emulsion.

In addition, each of the cosmetic compositions containing the compound represented by Chemical Formula 1 or 2 according to the present invention may further include components that are commonly contained in a general skin cosmetic product, for example, oils, water, surfactants, moisturizers, low molecular weight-alcohols, thickening agents, chelating agents, pigments, anti-septic agents, flavoring agents, etc., in suitable amounts.

A better understanding of the present invention may be obtained through the following examples which are set forth to illustrate, but is not to be construed as the limit of the present invention.

EXAMPLE 1

Synthesis of 2,3-O-dibenzyl-6-O-succinyl-ascorbic acid

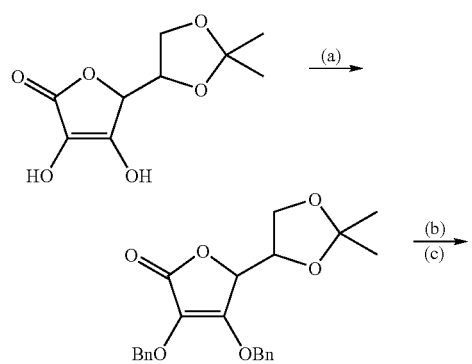

-continued

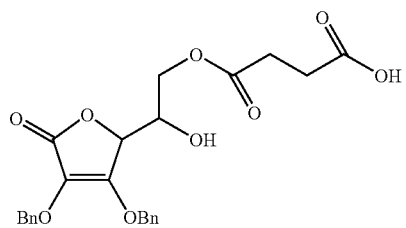

(a) 5,6-isopropylidiene-L-ascorbic acid (5 g, 23.1 mmol) was dissolved in 50 ml of dimethylformamide, and, to this solution, cesium hydrogen carbonate (15 g, 46 mmol) at a solid state was added. This mixture was added with benzyl chloride (7.3 g, 58 mmol) and then stirred at 50° C. for 4 hrs. From this reaction solution, the dimethylformamide was removed under pressure. The resulting concentrated solution was diluted with dichloromethane and filter to remove generated solids. The filtrate was then concentrated under pressure.

(b) The compound as prepared above was dissolved in dichloromethane and added with 20% (v/v) of TFA, followed by stirring for 4 hrs. From this reaction solution, the solvent and TFA were removed under pressure. The resulting solution was recrystallized, thus generating a light yellow semi-solid compound.

(c) The compound as prepared in (b) was dissolved in dimethylformamide and added with succinic acid (1.2 eq.). Then, triethylamine (1.2 eq.) was slowly added to the solution. After stirring for 16 hrs at room temperature, the dimethylformamide was removed from the mixture under pressure. The concentrated solution was subjected to silica gel column chromatography, thus yielding a light yellow semi-solid compound (3.9 g).

$^1$HNMR (CDCl$_3$) of the 2,3-O-dibenzyl-6-O-succinyl-ascorbic acid: 2.67 (s, 4H, CH2CH2COOH) 4.06 (t, 1H, C-5-H), 4.32 (d, 2H, C-6-H2), 4.67 (d, 1H, C-4-H), 5.17 (m, 4H, O—CH2-Ph), 7.36 (m, 10H, Ar—H)

EXAMPLE 2

Synthesis of 2-O-(3-hydroxypropyl)-3-O-benzyl-5,6-isopropylidiene-ascorbic acid

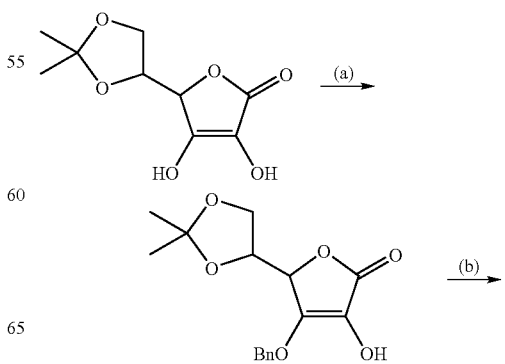

-continued

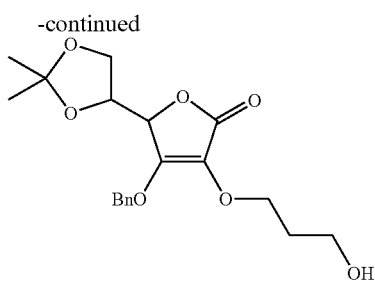

(a) 5,6-isopropylidiene-L-ascorbic acid (5 g, 23.1 mmol) was dissolved in 50 ml of dimethylformamide, and, to this solution, cesium hydrogen carbonate (3.8 g, 11.5 mmol) at a solid state was added. This mixture was added with benzyl chloride (1.45 g, 11.5 mmol) and then stirred at 50° C. for 16 hrs. From this reaction solution, the dimethylformamide was removed under pressure. The resulting concentrated solution was diluted with dichloromethane and filtered to remove generated solids. The filtrate was then concentrated under pressure.

(b) The compound as prepared above was dissolved in dimethylformamide and added with 3-bromopropanol (1 eq.) and cesium hydrogen carbonate (1 eq.) at a solid state, followed by stirring at 50° C. for 4 hrs. From the mixture, the dimethylformamide was removed under pressure. The resulting concentrated solution was subjected to silica gel column chromatography, thus yielding a white solid compound (2.9 g).

$^1$HNMR (CDCl$_3$) of the 2-O-(3-hydroxypropyl)-3-O-benzyl-5,6-isopropylidiene-ascorbic acid: 1.35 (s, 3H, C-C$\underline{H}$3), 1.39 (s, 3H, C-C$\underline{H}$3), 1.85 (m, 2H, O—CH2C$\underline{H}$2CH2-OH), 3.58 (t, 2H, O—CH2CH2C$\underline{H}$2-OH), 3.9(t, 2H, O—C$\underline{H}$2CH2CH2-OH), 3.98-4.24 (m, 3H, C-5-$\underline{H}$, C-6-$\underline{H}$2), 4.51 (d, 1H, C-4-$\underline{H}$), 5.17 (s, 2H, O—C$\underline{H}$2-Ph), 7.37 (m, 5H, Ar—$\underline{H}$)

EXAMPLE 3

Synthesis of Peptides

Peptides used in the present invention were prepared by solid phase peptide synthesis using Fmoc (9-fluorenylmethoxycarbonyl) as a protector of Nα-amino acids, and the peptide chain was elongated by a HOBt-DCC (N-hydroxybenzotriazole-dicyclohexylcarodiimide) method (Wang C. Chan, Perter D. white, "Fmoc solid phase peptide synthesis" Oxford). Glycyl-hystidyl-lysine, glycyl-lysyl-histidine, glycyl-proryl-hydroxyproline, lysyl-threonyl-threonyl-lysyl-serine (SEQ ID NO:1)peptides were synthesized.

EXAMPLE 4

Synthesis of Vitamin C Derivatives 4-1: Synthesis of a Compound of Chemical Formula 1

To each of the peptides synthesized in Example 3, coupled up to a N-terminal amino acid, a 20% (Piperidine/N-methylpyrrolidone) solution was added to remove the Fmoc groups. Then, the peptide was washed with N-methylpyrolidone and dichloromethane, and coupled with the vitamin C derivative synthesized in Example 1. The resulting peptide-coupled vitamin C derivative was washed several times with N-methylpyrolidone and dichloromethane and dried under nitrogen gas. The dried product was incubated in a mixture of trifluoroacetic acid: phenol: thioanisole: water: triisopropylsilane at a ratio of 85:5:5:3:2 (v/v) for 2 to 3 hrs to remove the peptide protection groups. The peptide coupled with vitamin C derivative was eluted from a resin onto which the peptide had been attached, and precipitated with diethylether. To eliminate the benzyl groups protecting the alcohol groups at carbon positions 2 and 3 of vitamin C, the precipitated peptide was treated with 10% Pd/C in methanol with stirring for about one hour at room temperature under a hydrogen atmosphere. Thereafter, the solution was filtrated over Celite to remove the Pd/C, concentrated under pressure, and purified by passage through a purified reverse phase high performance liquid chromatography column (Zobax, C8 300 Å, 21.1 mm×25 cm) using a gradient of acetonitrile in 0.1% trifluoroacetic acid to give a peptide-coupled vitamin C derivative of Chemical Formula 1.

4-2: Synthesis of a Compound of Chemical Formula 2

The vitamin C derivative synthesized in Example 2 and a C-terminal peptide side chains of which had been protected with triphenylmethane groups were dissolved in dimethylformamide and added with N-hydroxybenzotriazole. This mixture was added with N,N'-dicyclohexylcarbodiimide and stirred at room temperature for 2 hrs to couple the vitamin C derivative synthesized in Example 2 with the C-terminal peptide. From this reaction solution, the dimethylformamide was removed under pressure. The resulting concentrated solution was diluted with dichloromethane and added with 1% trifluoroacetic acid. The resulting mixture was stirred at room temperature for 10 min to remove the triphenylmethyl group as a protector of the side chain of the C-terminal peptide. Subsequently, the mixture was added with triethylamine and coupled to a chlorophenylmethyl resin. Thereafter, peptide elongation was carried out according to the same method as in Example 3. To the resulting vitamin C derivative coupled with the peptide coupled up to a N-terminal amino acid, a 20% (Piperidine/N-methylpyrrolidone) solution was added to remove Fmoc groups. Then, the peptide-coupled vitamin C derivative was washed with N-methylpyrrolidone and dichloromethane, and dried under nitrogen gas. The dried product was incubated in a mixture of trifluoroacetic acid: phenol: thioanisole: water: triisopropylsilane at a ratio of 85:5:5:3:2 (v/v) for 2 to 3 hrs to remove the peptide protection groups. The peptide coupled with vitamin C derivative was eluted from a resin onto which the peptide had been attached, and precipitated with diethylether. To eliminate the benzyl groups protecting the alcohol group at a carbon position 3 of vitamin C, the precipitated peptide was treated with 10% Pd/C in methanol with stirring for about one hour at room temperature under a hydrogen atmosphere. Thereafter, the solution was filtrated over Celite to remove the Pd/C, concentrated under pressure, and purified by passage through a purified reverse phase high performance liquid chromatography column (Zobax, C8 300 Å, 21.1 mm×25 cm) using a gradient of acetonitrile in 0.1% trifluoroacetic acid to give a peptide-coupled vitamin C derivative of Chemical Formula 2.

Each of the peptide-coupled vitamin C derivatives as prepared above was evaluated for its molecular weight using mass spectrophotometer to investigate the coupling of the peptide with the vitamin C having a succinyl or propyl group. Table 1, below, summarizes the measured molecular weights of the vitamin C derivatives synthesized in Example 4.

TABLE 1

| Compound Nos. | Peptides | X | MWs measured by MS Theoretical | MWs measured by MS Measured |
|---|---|---|---|---|
| I-1 | GHK | —OC(O)CH$_2$CH$_2$C(O)— | 601.38 | 602 |
| I-2 | GKH | —OC(O)CH$_2$CH$_2$C(O)— | 601.38 | 602 |
| I-3 | GPO | —OC(O)CH$_2$CH$_2$C(O)— | 545.31 | 546 |
| I-4 | KTTKS | —OC(O)CH$_2$CH$_2$C(O)— | 821.50 | 822 |
| II-1 | GHK | —OC(O)CH$_2$CH$_2$C(O)— | 601.38 | 602 |
| II-2 | GKH | —OC(O)CH$_2$CH$_2$C(O)— | 601.38 | 602 |
| II-3 | GPO | —OC(O)CH$_2$CH$_2$C(O)— | 545.31 | 546 |
| II-4 | KTTKS | —OC(O)CH$_2$CH$_2$C(O)— | 821.50 | 822 |
| III-1 | GHK | —OC(O)CH$_2$CH$_2$C(O)— | 601.38 | 602 |
| III-2 | GKH | —OC(O)CH$_2$CH$_2$C(O)— | 601.38 | 602 |
| III-3 | GPO | —OC(O)CH$_2$CH$_2$C(O)— | 545.31 | 546 |
| III-4 | KTTKS | —OC(O)CH$_2$CH$_2$C(O)— | 821.50 | 822 |
| IV-1 | GHK | —CH$_2$CH$_2$CH$_2$O— | 556.39 | 557 |
| IV-2 | GKH | —CH$_2$CH$_2$CH$_2$O— | 556.39 | 557 |
| IV-3 | GPO | —CH$_2$CH$_2$CH$_2$O— | 545.31 | 546 |
| IV-4 | KTTKS | —CH$_2$CH$_2$CH$_2$O— | 779.53 | 780 |

The compound numbers shown in Table 1, I, II, III and IV, represents compounds of Chemical Formula 1a, 1b, 1c and 2, respectively.

$^1$H NMR (CD$_3$OD) of the compound II-1: 8.78(dd, 1H), 7.38(s, 1H), 4.73(m, 3H), 4.42(m, 1H), 4.27(m, 2H), 4.14(m, 1H), 3.84(m, 2H), 3.19(m, 1H), 2.96(td, 2H), 2.76(m, 2H), 2.59(m, 2H), 1.81(m, 4H), 1.50(m, 2H)

$^1$H NMR (CD$_3$OD) of the compound II-2: 8.78(m, 1H), 7.36(s, 1H), 4.74(m, 3H), 4.24(m, 3H), 3.86(d, 2H), 3.29(m, 2H), 2.95(t, 2H), 2.66(m, 4H), 1.80(m, 4H), 1.51(m, 2H)

$^1$H NMR (CD$_3$OD) of the compound II-4: 4.78(m, 3H), 4.31(m, 10H), 3.90(m, 2H), 2.96(q, 4H), 2.65(m, 4H), 1.92 (m, 2H), 1.74(m, 6H), 1.52(m, 4H), 1.23(q, 6H)

EXPERIMENTAL EXAMPLE 1

Color Change Test

The compounds I to IV synthesized in Example 4 and vitamin C (Sigma Aldrich) were independently dissolved in 50 mM potassium phosphate of pH 7.0 at a concentration of 50 mM, and stored in an incubator at 40° C. for three weeks. Thereafter, the compounds and vitamin C were evaluated for color change according to the standard criteria, and the results are given in Table 2, below.

TABLE 2

| Compounds | After 1 week | After 2 weeks | After 3 weeks |
|---|---|---|---|
| Vitamin C | + | +++ | ++++ |
| I-1 | − | + | + |
| I-2 | − | + | + |
| I-3 | − | + | + |
| I-4 | − | + | + |
| II-1 | − | + | + |
| II-2 | − | + | + |
| II-3 | − | + | + |
| II-4 | − | + | + |
| III-1 | − | + | + |
| III-2 | − | + | + |
| III-3 | − | + | + |
| III-4 | − | + | + |
| IV-1 | − | + | ++ |
| IV-2 | − | + | ++ |

TABLE 2-continued

| Compounds | After 1 week | After 2 weeks | After 3 weeks |
|---|---|---|---|
| IV-3 | − | + | ++ |
| IV-4 | − | + | ++ |

−: no or very slight noticeable change (colorless or light yellow);
+: slight;
++: moderate;
+++: extreme As shown in Table 2, the compounds I to IV of the present invention were found to be relatively stable in comparison with the vitamin C showing a severe change in color after three weeks. Also, during the storage of three weeks, in case of the present compounds, no precipitates were detected.

EXPERIMENTAL EXAMPLE 2

Evaluation of Inhibitory Activity Against Tyrosinase

The compounds II-1, II-2 and II-4, synthesized in Example 4, were evaluated for inhibitory activity against tyrosinase. Tyrosinase was purchased from the Sigma Company, which was isolated from mushrooms and purified. Tyrosin as a substrate for the purified mushroom tyrosinase was prepared by dissolving in 0.05 M potassium phosphate buffer (pH 6.8) in an amount of 0.3 mg/ml. The compounds and vitamin C were dissolved in distilled water at a concentration of 10 mM, and diluted with distilled water to suitable concentrations.

0.5 ml of the tyrosine solution and 0.5 ml of a buffer were put into a test tube, and 0.5 ml of the diluted compound or vitamin C was added to the test tube. After each test tube was incubated in an incubator at 37° C. for 10 min, 0.05 ml of tyrosinase (2,000 U/ml) was added to each test tube, followed by incubation at 37° C. for 10 min. A sample added with 0.5 ml distilled water instead of the compound was used as a control. Thereafter, each test tube was rapidly cooled on ice to terminate the reaction. Absorbance at 475 nm was measured using a spectrophotometer. Inhibition rate against tyrosinase was calculated using the measured absorbance according to the following Equation 1, and IC$_{50}$ values (compound concentration to inhibit 50% of tyrosinase activity) were then determined.

$$\text{Inhibition rate (\%)} = (A - B)/A \times 100 \qquad \text{Equation 1}$$

wherein, A is an absorbance at 475 nm of a sample not containing an inhibitor, and B is an absorbance at 475 nm of a sample containing an inhibitor.

TABLE 3

| Compounds | IC$_{50}$ |
|---|---|
| Vitamin C | 350 μM |
| II-1 | 650 μM |
| II-2 | 700 μM |
| II-4 | 350 μM |

EXPERIMENTAL EXAMPLE 3

Evaluation of Inhibitory Activity on Melanin Synthesis

B16 melanocytes (Korean Cell Line Bank, KCLB) were grown in culture dishes. After culture media were removed, various concentrations of each of the compounds (vitamin C, arbutin, and the compounds II-1, II-2 and II-4) were added to the culture dishes. After incubation at 37° C. under 5% $CO_2$ for a predetermined time, the culture medium was removed from each dish, and the cells were washed with PBS (phosphate buffered saline) and recovered by trypsin treatment. The collected cells were counted using a hematocytometer, and centrifuged at 5,000 to 10,000 rpm for 10 min. After the supernatant was discarded, the cell pellet was dried at 60° C. and treated with 100 μl of 1 M sodium hydroxide containing 10% DMSO or a proper amount of a cell lysis buffer, melanin in the cell were obtained in an incubator at 60° C. To investigate melanin levels, absorbance for the cell lysate was measured at 490 nm using a microplate reader. For each sample, a melanin level per predetermined cell number or protein concentration was determined, and the results are given in FIG. 1.

As shown in FIG. 1, in a concentration of 1 mM, the compound II-4 exhibited inhibitory activity on melanin production by B16 melanocytes higher by about 24% than arbutin and higher by about 10% to 20% than vitamin C. Also, the compound II-1 displayed inhibitory activity similar to that of the compound II-4.

EXPERIMENTAL EXAMPLE 4

Evaluation of Inhibitory Activity Against Elastase

Elastase activity was evaluated by photometrically measuring ρ-nitroaniline generated by elastase (Sigma) using MeO-Suc-(Ala)2-Pro-Val-pNA as a substrate. The results are given in FIG. 2.

Figure 2:
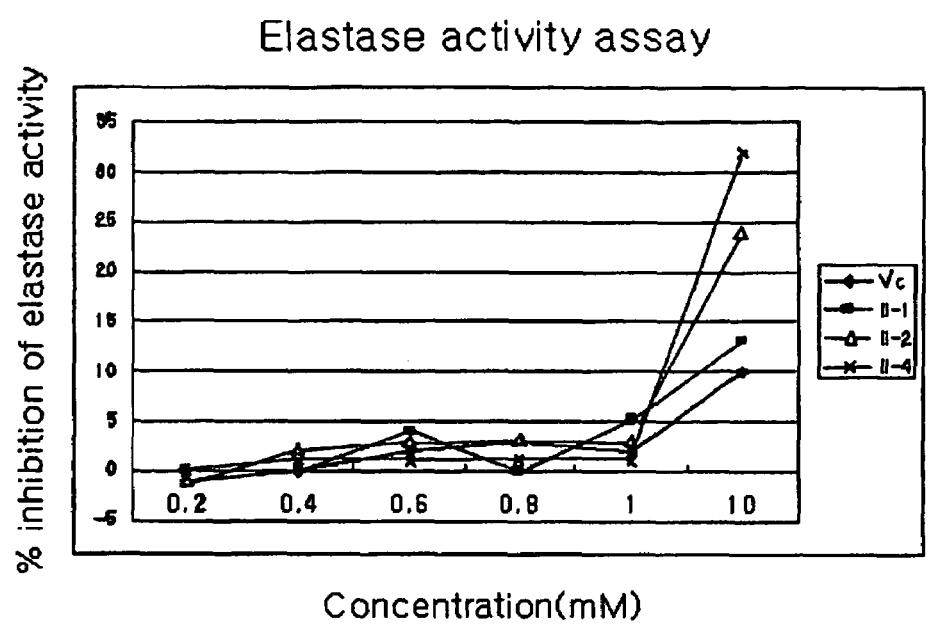
FIG. 2 is a graph showing the effects of the compounds of the present invention and vitamin C on elastase activity.

As shown in FIG. 2, at concentrations of less than 1 mM, the compounds of the present invention displayed no large difference with vitamin C in inhibitory activity against elastase. However, at concentrations of higher than 1 mM, the compounds of the present invention exhibited about 2% to 20% higher inhibitory activity against elastase than vitamin C.

EXPERIMENTAL EXAMPLE 5

Evaluation of Cytotoxicity

In order to investigate primary safety of the compounds of the present invention as cosmetic materials, MTT assay (Mossman T., 1983, Journal of Immunological Methods 65, 55-63) was carried out in human normal fibroblasts, B16 melanocytes and HaCaT cells, wherein the cells were treated with various concentrations of the compounds II-1, II-2 and II-4. As a result, even at a concentration of 5 mM, the compound II-4 did not showed cytotoxicity. Also, the compounds II-1 and II-2 showed behavior similar to vitamin C in cytotoxicity in concentrations of less than 10 mM. These results indicate that the compounds of the present invention are very safe upon topical application to the skin.

EXPERIMENTAL EXAMPLE 6

Skin Irritation Test

A skin irritation test for the compound II-4 was carried out by a patch test on rabbits (Draize J. H. et al., 1944, J. Pharmacol. Exp. Ther., 82: 377-390; Gfeller W et al., 1985, Fd. Chem. Toxic., 23: 165-168; Bosshard, E et al., 1985, Fd. Chem. Toxic., 12:149-154).

0.5 ml of 1% compound II-4 in 0.01M PBS was applied to each hairless area (2.5 cm×2.5 cm) of the back of rabbits for 24 hrs once. Each of the treated sites was covered with a single sheet of gauze (10 cm×10 cm) to prevent loss of the test compound by contact and then an impermeable and unreactive solid film to prevent evaporation of the test compound. Then, the treated site was bound with an elastic bandage while not disturbing behavior of the rabbits, and the bandage was then held in place by a paper tape. 24 hrs and 72 hrs after application of the test compound, skin irritation was investigated. As a result, the compound II-4 was found to be very safe upon application to the skin.

EXPERIMENTAL EXAMPLE 7

Ocular Irritation Test

The compound II-4 was determined whether inducing ocular irritation or evaluated for the degree of ocular irritation. The compound II-4 was applied to the eyes of rabbits (New Zealand White Rabbit, NZW).

0.1 ml of 1% compound II-4 in 0.01M PBS was applied to the eyes of the rabbits. That is, the test compound was applied to one eye (right) of each of nine rabbits in an amount of 0.1 ml/head according to the standard criteria for toxicity test of pharmaceutical and medicinal substances (a publication by Korean Food & Drug Administration, Vol. 1999-61, Dec. 22, 1999). After application of the test compound, the treated eyes of the rabbits were maintained at a state of being closed for about one second to prevent loss of the applied test compound. Then, the degree of damage in the cornea, the iris and the conjunctiva was investigated. From day 1 to day 7, no sign of conjunctiva redness and chemosis was observed. In addition, all of rabbits treated with the test compound displayed an Index of Acute Ocular Irritation (I.A.O.I) of zero. These results demonstrate that the compound II-4 has no harmful effect on the eyes.

EXPERIMENTAL EXAMPLE 8

Skin Sensitization Test

A skin irritation test for the compound II-4 was carried out by a GPMT (Guinea Pig Maximization Test) using male Hartley guinea pigs (SamtakoBioKorea, Co. Ltd.). The GPMT is widely used for the identification of a chemical for cosmetic use or other substances for a potential skin sensitizer to induce contact allergy.

The compound II-4 prepared at 1% concentration was intradermally injected to the cervical and dorsal skin of the guinea pigs in an amount of 0.1 ml/site. After this primary sensitization, a patch that had been loaded with 1 ml or 0.2 ml per animal of the 1% compound II-4 was placed over the sites of the intradermal injection, and left in place at an occluded state for 48 hrs (secondary sensitization). Two weeks after secondary sensitization, topical challenge was carried out, as follows. A patch that had been loaded with the 1% compound II-4 was applied to induced regions of the left abdominal skin of the guinea pigs and left in place at an occluded state for 24 hrs. Skin reading was made after removal of the patches. The results are given in Table 4, which includes the data for sensitization class for skin reactions after the topical challenge.

TABLE 4

| Group/test substance | Test period (hrs) | Sensitization score (total hrs) | Sensitization rate (%) | Sensitization class |
|---|---|---|---|---|
| G1/0.01M PBS | 24 | 0 | 0 (0/5) | I (Very weak) |
| G2/II-4 | 24 | 0 | 0 (0/10) | I (Very weak) |
| G3/0.1% CDNB | 24 | 3 | 100 (5/5) | V (Extreme) |
| G1/0.01M PBS | 48 | 0 | 0 (0/5) | I (Very weak) |
| G2/II-4 | 48 | 0 | 0 (0/10) | I (Very weak) |
| G3/0.1% CDNB | 48 | 3 | 100 (5/5) | V (Extreme) |

PBS: Phosphate buffered saline
CDNB: 1-chloro-2,4-dinitrobenzen

As shown in Table 4, in the group 2 treated with the compound II-4, no skin reaction was observed in all of the induced regions of ten guinea pigs. In addition, the compound II-4 showed a skin irritation rate of 0%, and thus evaluated as sensitization class I (very weak). These results indicate that the compound II-4 does not induce skin sensitization.

EXPERIMENTAL EXAMPLE 9

Phototoxicity Test

Twenty male Hartley guinea pigs were divided into four groups each which consisted of five guinea pigs: a control group (0.01 M PBS), a treatment group (the compound II-4), a positive control group 1 (Chlorpromazine, CP) and another positive control group 2 (8-methoxypsoralen, 8-MOP). Each of the test samples was applied to the skin of guinea pigs, and the guinea pigs were exposed to ultraviolet A (UVA) radiation. Then, potency to induce phototoxicity was evaluated. Induction of phototoxicity, which is an abnormal response of the skin to a photo-stimulus such as ultraviolet or visible light, occurs non-immunologically by a chemical. Unlike the allergic response, the degree of phototoxicity can be expected by sufficient intensity of radiation and drugs.

The compound II-4 was prepared at various concentrations of 0.1%, 0.5%, and 1% using 0.01 M PBS as an excipient. CP and 8-MOP were prepared at a final concentration of 10% in DMSO and then diluted to 1%. Each of guinea pigs was fixed on a fixing plate, and the skin of the guinea pig was covered with 50 μl of each of the test samples. Then, the right area of the skin was not exposed to UV light, and the left area of the skin was exposed to UVA light (320 to 380 nm) of 15 J/cm$^2$, which was irradiated in a distance of about 10 cm for about 2 hrs. 24 hrs, 48 hr and 72 hrs after UVA irradiation, photosensitization in the treatment group was evaluated in comparison with that in the positive control groups. The results are given in Table 5, below. As shown in Table 5, the compound II-4 was found to rarely have phototoxicity.

TABLE 5

| | | | Areas not exposed to UVA | | | Areas exposed to UVA | | |
|---|---|---|---|---|---|---|---|---|
| Group/test material | N | A.C.* (%) | Total score/ Site No.[a] | Mean score | Evaluation | Total score/ Site No | Mean score | Evaluation |
| G1/WFI | 5 | 0 | 0 + 0/10 | 0 | Practically non-irritating | 0 + 0/10 | 0 | Practically non-irritating |
| | | 0 | 0 + 0/10 | 0 | Practically non-irritating | 0 + 0/10 | 0 | Practically non-irritating |
| | | 0 | 0 + 0/10 | 0 | Practically non-irritating | 0 + 0/10 | 0 | Practically non-irritating |
| G2/II-4 | 5 | 0.1 | 0 + 0/10 | 0 | Practically non-irritating | 0 + 0/10 | 0 | Practically non-irritating |
| | | 0.5 | 0 + 0/10 | 0 | Practically non-irritating | 0 + 0/10 | 0 | Practically non-irritating |
| | | 1 | 0 + 0/10 | 0 | Practically non-irritating | 0 + 0/10 | 0 | Practically non-irritating |
| G3/CP | 5 | 0.1 | 0 + 0/10 | 0 | Practically non-irritating | 7 + 2/10 | 0.9 | Minimum irritating |
| | | 1 | 0 + 0/10 | 0 | Practically non-irritating | 12 + 10/10 | 2.2 | Clearly irritating |
| | | 10 | 0 + 0/10 | 0 | Practically non-irritating | 13 + 12/10 | 2.5 | Extremely irritating |
| G4/8-MOP | 5 | 0.1 | 0 + 0/10 | 0 | Practically non-irritating | 12 + 11/10 | 2.3 | Clearly irritating |
| | | 1 | 8 + 6/10 | 1.4 | Clearly irritating | 16 + 16/10 | 3.2 | Extremely irritating |
| | | 10 | 10 + 8/10 | 1.4 | Clearly irritating | 20 + 20/10 | 4.0 | Extremely irritating |

N: animal No.; CP: Chlorpromazine; 8-MOP: 8-methoxypsoralen; WFI: Water For Injection;
*Applied Concentration;
[a] ΣTotal highest possible erythema/eschar score + ΣTotal highest possible edema score/No. of erythema/eschar observation-site (5) + No. of edema observation-site (5) = 10

EXPERIMENTAL EXAMPLE 10

Toxicity Test Upon Single Administration

The compound II-4 was evaluated for safety upon single oral administration. The compound II-4 was orally administered to five male and five female mice (SamtakoBioKorea Co. Ltd.) in a single dose of 2,000 mg/10 ml/kg. As a control, five male and five female mice were orally administered once with 0.1 M PBS of 10 ml/kg. During 14 days after administration, death, general pathogenic symptoms and change in body weight were not observed. The compound II-4 was found that doses of higher than 2,000 mg/kg is lethal to both male and female mice.

EXPERIMENTAL EXAMPLE 11

Photosensitization Test

A photosensitization test for the compound II-4 was carried out according to an Adjuvant & Strip method using male Hartley guinea pigs.

After four sites to be sensitized were selected at the cervical and dorsal skin of the guinea pigs, an emulsion of WFI and FCA were intradermally injected to each of the selected sites. The sensitized sites were stripped only in a degree of inducing weak erythema, and covered with 0.01 PBS (excipient group), the compound II-4 (test group) and CP (chlorpromazine; positive control group) in a non-occlusive manner. After two hours, long wave-length UV light of about 10 J/cm$^2$ was irradiated to the test substance-applied sites. 24 hrs, 48 hrs and 72 hrs after UV irradiation, signs of photosensitization were investigated.

In both the excipient and test groups, the skin regions exposed to UVA or not were evaluated to have irritation indexes of "zero" and photosensitivity indexes of "zero" (practically non-irritating). In case of the positive group, the UVA-unexposed skin regions were evaluated to have irritation indexes of "zero", while the UVA-exposed skin regions were evaluated to have irritation indexes of "5.8" (extremely irritating), indicating that the guinea pigs used in this test normally response to the photosensitizer CP. During the test period, no general pathogenic symptoms and death were observed, as well as no significant change in body weight was observed. The test results are given in Table 6.

As apparent from the data shown in Table 6, the compound II-4 was found to be not a photosensitizer.

EXPERIMENTAL EXAMPLE 12

Effect on Collagen Biosynthesis

The effective component of the present invention was evaluated whether stimulating collagen synthesis, and this test was carried out using human normal fibroblasts.

Collagen synthesis was measured by a modification of a method as described in a publication described by Martens, Gut, 1992, 33, 1664-1670. In case of the cells not treated with any test substance, their collagen levels were designated "100%". This assay will be described in detail, below.

Human normal fibroblasts were aliquotted onto 6-well plates for cell culturing, and grown in culture medium containing 0.05% FBS (Fetal Bovine Serum) for 48 hrs. Thereafter, the cells were washed with PBS twice. For each well, cells and a culture fluid were independently divided into two aliquots. Of two aliquots, only one aliquot was treated with collagenase, and proteins were then precipitated using TCA (trichloroacetic acid). The effect of the compound II-4 on collagen synthesis was determined based on the difference between the collagenase-treated and collagenase-untreated samples in radioactivity. In case of the cells not treated with any test substance, as described above, their collagen levels were expressed as "100%".

Figure 3:
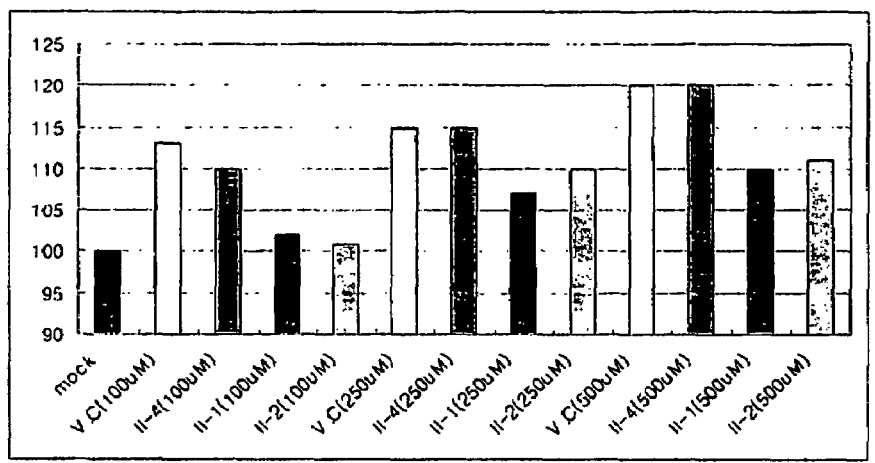
FIG. 3 is a graph showing the effects of the compounds of the present invention and vitamin C on collagen biosynthesis.

As shown in FIG. 3, the compound II-4 was found to have similar stimulatory effect on collagen synthesis to vitamin C. These results indicate that the compound II-4 has excellent stimulatory effect on collagen synthesis, as well as improved stability that was demonstrated in the color change test of Experimental Example 1.

EXPERIMENTAL EXAMPLE 13

Antioxidant Effect

The compounds II-1, II-2 and II-4, prepared in Example 4, were evaluated for free radical-scavenging ability. The free radical scavenging ability of the compounds was carried out by measuring optimal density (O.D.) using a DPPH (1,1-diphenyl-2-picrylhydrazyl) free radical, which shows color-change according to oxidation/reduction environments.

TABLE 6

| Group/test substance | N | Areas not exposed to UVA | | Areas exposed to UVA | | Photosensitization index[b] |
|---|---|---|---|---|---|---|
| | | Mean score | Stimulation index[a] | Mean score | Stimulation index[a] | |
| G1/0.01M PBS | 8 | (0 + 0)/5 | 0 | (0 + 0)/5 | 0 | 0 (Practically non-irritating) |
| G2/II-4 | 5 | (0 + 0)/5 | 0 | (0 + 0)/5 | 0 | 0 (Practically non-irritating) |
| G3/CP | 5 | (0 + 0)/5 | 0.0 | (16 + 13)/5 | 5.8 | 5.8 (Extremely irritating) |

[a](ΣMax. score of erythema and eschar + ΣMax. score of edema)/Number of animals;
[b]Irritating index of UVA irradiation site - Irritation index of non-irradition site;
PBS: phosphate buffered saline;
CP: chlorpromazine;
N: animal No.

100 μl of each of the compounds, dissolved in distilled water or solvent, was added with 100 μl of 200 μM DPPH. After the mixture was well mixed and incubated at room temperature for 10 min, absorbance was measured at 517 nm. Distilled water or the solvent excluding the compounds was used as a control.

Figure 4:
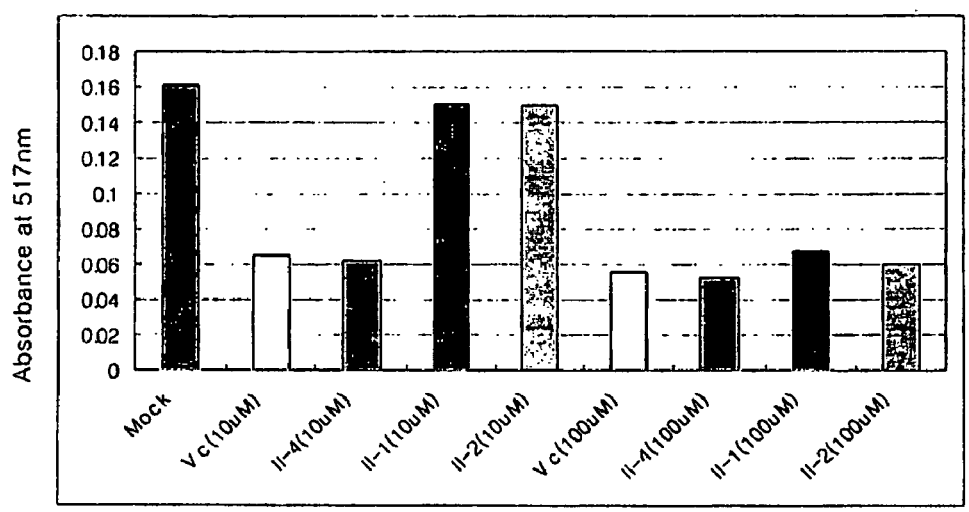
FIG. 4 is a graph showing the free radical scavenging ability of the compounds of the present invention and vitamin C.

As shown in FIG. 4, at a concentration of 10 μM, the compound II-4 displayed an ability to scavenge 70% or higher of the free radical, and this free radical scavenging ability was found to be similar to that of vitamin C. At a concentration of 100 μM, the compounds II-1 and II-2 exhibited an ability to scavenge 70% or higher of the free radical. These results indicate that the compound II-4 has antioxidant effect similar to vitamin C that is known to have an excellent antioxidant effect.

As described herein before, the vitamin C derivatives of the present invention have improved stability, safety and percutaneous permeability without side effects such as skin irritation. Therefore, the vitamin C derivatives of the present invention are applicable for enhancing skin states or inhibiting the skin states to get worse.

Although a preferred embodiment of the present invention has been described for illustrative purposes, those skilled in the art will appreciate that various modifications, additions and substitutions are possible, without departing from the scope and spirit of the invention as disclosed in the accompanying claims.

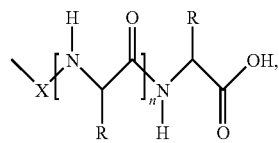

but both are not —OH simultaneously, wherein

X represents —OC(O)(CH$_2$)$_m$C(O)—,

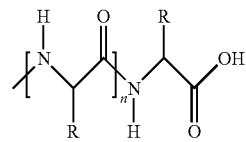

is a peptide in which identical or different amino acid residues selected from glycine, lysine, histidine, serine, proline, hydroxyproline and threonine are joined by amide linkages, R is a side chain of each of the amino acid residues selected from glycine, lysine, histidine, serine, proline, hydroxyproline and threonine,

---

---

What is claimed is:

1. A vitamin C derivative represented by Chemical Formula 1, below, or a pharmaceutically acceptable salt thereof:

[Chemical Formula 1]

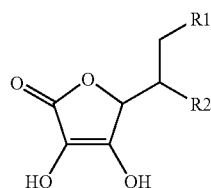

wherein, R1 and R2, which are identical or different, each represent —OH or n is an integer of 2 to 9, and m is an integer of 2 to 5.

2. The vitamin C derivative according to claim 1, wherein the n is an integer of 3 to 5, and the m is an integer of 2; or the pharmaceutically acceptable salt thereof.

3. The vitamin C derivative according to claim 2, wherein the moiety

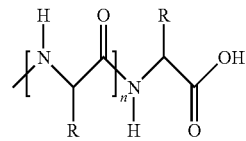

is selected from glycyl-histidyl-lysine, glycyl-lysyl-histidine, glycyl-prolyl-hydroxyproline and lysyl-threonyl-threonyl-lysyl-serine (SEQ ID NO:1); or the pharmaceutically acceptable salt thereof.

4. The vitamin C derivative according to claim 3, wherein the vitamin C derivative is selected from 6-(succinyl-lysyl-threonyl-threonyl-lysyl-serine) (SEQ ID NO:1) ascorbic acid, 6-(succinyl-glycyl-lysyl-histidine)ascorbic acid, and 6-(succinyl-glycyl-histidyl-lysine)ascorbic acid; or the pharmaceutically acceptable salt thereof.

5. A vitamin C derivative represented by Chemical Formula 2, below, or a pharmaceutically acceptable salt thereof:

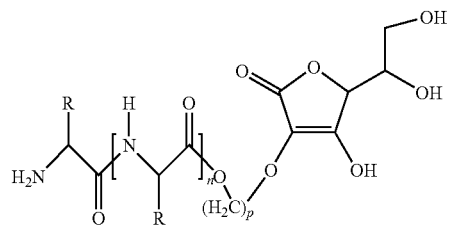

wherein

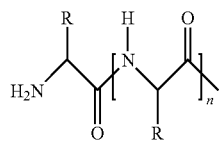

is a peptide in which identical or different amino acid residues selected from glycine, lysine, histidine, serine, proline, hydroxyproline and threonine are joined by amide linkages, R is a side chain of each of the amino acid residues selected from glycine, lysine, histidine, serine, proline, hydroxyproline and threonine, n is an integer of 2 to 9, and p is an integer of 2 to 5.

6. The vitamin C derivative according to claim 5, wherein the n is an integer of 3 to 5, and the p is an integer of 3; or the pharmaceutically acceptable salt thereof.

7. The vitamin C derivative according to claim 6, wherein the

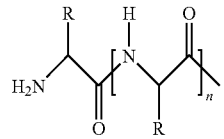

is selected from glycyl-histidyl-lysine, glycyl-lysyl-histidine, glycyl-prolyl-hydroxyproline and lysyl-threonyl-threonyl-lysyl-serine (SEQ ID NO:1); or the pharmaceutically acceptable salt thereof.

8. A composition for topical application to the skin, comprising a) the vitamin C derivative or the pharmaceutically acceptable salt thereof of claim 1 or 5 as an active ingredient; and b) a pharmaceutically or cosmetically acceptable carrier.

9. The composition according to claim 8, wherein the composition is used for cosmetics.

* * * * *

SEQUENCE LISTING

<160> NUMBER OF SEQ ID NOS: 1

<210> SEQ ID NO 1
<211> LENGTH: 5
<212> TYPE: PRT
<213> ORGANISM: Artificial Sequence
<220> FEATURE:
<223> OTHER INFORMATION: Synthetic

<400> SEQUENCE: 1

Lys Thr Thr Lys Ser
1               5